United States Patent
Redding, Jr.

[11] Patent Number: 6,149,953
[45] Date of Patent: *Nov. 21, 2000

[54] SEEDED MICROCAPSULES

[75] Inventor: Bruce K. Redding, Jr., Philadelphia, Pa.

[73] Assignee: Delta Food Group, Inc., Aston, Pa.

[ * ] Notice: This patent issued on a continued prosecution application filed under 37 CFR 1.53(d), and is subject to the twenty year patent term provisions of 35 U.S.C. 154(a)(2).

[21] Appl. No.: 09/111,897

[22] Filed: Jul. 8, 1998

Related U.S. Application Data

[63] Continuation of application No. 08/908,232, Aug. 7, 1997, abandoned, which is a continuation of application No. 08/576,636, Dec. 21, 1995, abandoned, which is a continuation of application No. 08/137,439, Nov. 8, 1993, abandoned

[60] Provisional application No. 60/082,165, Apr. 17, 1998.

[51] Int. Cl.$^7$ ....................................................... A21D 2/00
[52] U.S. Cl. ............................ 426/98; 426/96; 426/289; 426/295; 426/649; 426/653
[58] Field of Search .................................. 426/96, 98, 97, 426/295, 289, 649, 648, 653

[56] References Cited

U.S. PATENT DOCUMENTS

| | | | |
|---|---|---|---|
| 2,978,331 | 4/1961 | Ferrari | 99/91 |
| 3,622,350 | 11/1971 | Hammes | 99/143 |
| 3,959,496 | 5/1976 | Jackel | 425/25 |
| 4,572,833 | 2/1986 | Pedersen | 424/20 |
| 4,574,080 | 3/1986 | Roswall | 424/20 |
| 4,842,863 | 6/1989 | Nishimura | 424/438 |
| 5,178,894 | 1/1993 | Rudel | 426/549 |
| 5,271,945 | 12/1993 | Yoshioka | 424/489 |
| 5,595,762 | 1/1997 | Derrieu | 424/490 |
| 5,652,220 | 7/1997 | Heya | 424/490 |
| 5,716,640 | 2/1998 | Kamei | 424/451 |
| 5,723,269 | 3/1998 | Akagi | 424/497 |
| 5,814,342 | 9/1998 | Okada | 424/493 |
| 5,974,810 | 11/1999 | Speronello | 62/66 |

*Primary Examiner*—Carolyn Paden
*Attorney, Agent, or Firm*—Synnestvedt & Lechner LLP

[57] ABSTRACT

Microcapsules comprising a core surrounded by a shell having seeding agents disposed therein for the purpose of imparting enhanced or unique structural and/or functional characteristics to the microcapsules is disclosed. The seeding agents may be completely imbedded within the shell material or may protrude through the shell's surface to afford the microcapsule with diverse strength, thermal stability, weight, balance, buoyancy and dissolution characteristics as well as enhanced fluid dynamic properties. In another embodiment of the invention both imbedded and protruding seeding agents are employed. An example of a seeding microcapsule of the present invention is disclosed comprising an encapsulated salt composition having ascorbic acid seeds dispersed within an inert, thermoplastic shell for use in baking bromate-free bakery products such as bread.

14 Claims, 1 Drawing Sheet

SEEDED MICROCAPSULES

This application is a continuation of U.S. application Ser. No. 08/908,232, filed Aug. 7, 1997, now abandoned, which is a continuation of U.S. application Ser. No. 08/576,636, filed Dec. 21, 1995, now abandoned, which is a continuation of U.S. application Ser. No. 08/137,439, filed Nov. 8, 1993, now abandoned also claims the benefit U.S. Provisional No. 60/082,165 filed Apr. 17, 1998.

FIELD OF THE INVENTION

This invention is related to microcapsules which are used for a variety of purposes. In particular, the invention relates to a microcapsules comprised of a core encompassed by a shell, the shell having particles or "seeds" imbedded therein.

BACKGROUND OF THE INVENTION

Microcapsules are widely used in the pharmaceutical industry as well as in various food compositions. In general, an outer shell is used to protect an inner core material. Some microcapsules are designed so that the shell will release the core at some predetermined point in time. The shells of such microcapsules are made of various materials, selected based upon specific chemical and/or physical properties which will be exploited to cause release of core material as desired. For example, the hardness of the material used for the shell may be of primary interest in designing a microcapsule which will be released when the microcapsule is subjected to certain compression loads. In other instances, the shell material may be selected based upon its solubility characteristics, or melting point.

SUMMARY OF THE INVENTION

The subject invention relates to the addition of one or more seeding agents within the shell layer of a microcapsule to impact enhanced or unique structural and/or functional characteristics to the products. These seeding agents may be completely imbedded within the shell material or may protrude through the shell's surface to afford the microcapsule with diverse strength, thermal stability, weight, balance, buoyancy and dissolution characteristics as well as enhanced fluid dynamic properties. In another embodiment of the invention, both imbedded and protruding seeding agents are employed.

An example of a seeded microcapsule of the present invention is an encapsulated salt composition, for use in baking bromate-free bakery products such as bread, having ascorbic acid seeds dispersed within an inert, thermoplastic shell.

Bread is made commercially in the United States by either of three basic procedures: (1) the straight-dough method; (2) the sponge-and-dough method; or (3) the liquid sponge method. In the straight-dough method, all of the essential ingredients of the bread (flour, yeast, salt and water) are mixed together in a single step to form a dough which is fermented, placed into individual pans, proofed and baked. In the sponge-and-dough method, the yeast, water and 50–70% by weight of the flour are formed into an initial dough which is referred to as the "sponge". The sponge is fermented for 2–4 hours after which the remaining portion of the flour, salt and secondary additives are added to form a final dough. The final dough is then placed into individual baking pans, proofed and baked. The liquid sponge method differs from the sponge-and-dough method mainly in that the sponge is of liquid consistency and contains 10–60% by weight of the total flour. [The term "proofing" or "proofed" refers to the practice of subjecting dough to storage for about one hour at a temperature of 90°130° F. and high humidity (60–90% rh) in order to restore the extensibility and aeration of the dough prior to baking.]

In addition to the essential four components, it is customary to add one or more secondary additives, which are optional. The use of these materials is in large part a function of the particular bread being made. Such secondary additives include yeast foot, sweeteners, shortening, dairy blend, protease enzyme, emulsifiers, dough strengtheners, preservatives, gluten, etc. For example, a typical bread may contain as secondary additives all of the following: high fructose corn syrup; wheat gluten; soybean oil; calcium propionate; potassium bromate; vinegar; ammonium sulfate; calcium sulfate; ascorbic acid; and sodium stearoyl lactylate.

Among the most commonly used and preferred secondary additives are oxidizing agents such as potassium bromate ($KBrO_3$), which, then added to the dough at levels up to 75 ppm by weight, reacts with the gluten, or protein, fraction of the wheat to improve the strength and resiliency of the dough. A substantial portion of this strengthening action occurs in the first several minutes the bread is in the baking oven as increased temperature accelerates the action of potassium bromate. Also during this first portion of the baking process the dough expands considerably in volume due to accelerated gas production by the yeast and expansion of the contained gas with increasing temperature.

The strengthening action of potassium bromate works in conjunction with this volume expansion to "set" the structure of the dough into a loaf of desired volume and consistency. This synergistic action is especially valued in modern automated production lines where mechanical shock can cause a reduction in dough volume prior to entering the baking oven. Therefore, breads which do not contain potassium bromate or an equivalent oxidizing agent tend to have poor volume, weak crust, poor symmetry and uneven grain and texture.

However, recent studies in Japan and in the United Kingdom indicate that potassium bromate may not be completely converted to harmless potassium bromide during the baking process. Moreover, it is believed that residual amounts of bromate may be carcinogenic. Therefore, the use of potassium bromate as a component of bread is being curtailed or even discontinued.

For the above reasons, there is a need for a convenient, safe, and effective means of replacing potassium bromate in yeast raised baked goods. In this regard, ascorbic acid (Vitamin C) has been mentioned. Though the functions of ascorbic acid in baking are the same as potassium bromate, it has significant disadvantage that it is substantially decomposed by the moisture, oxygen, trace metals, and pH conditions present during the mixing and proofing, leaving little or none remaining to work with the volume expansion that occurs in the oven. This makes it unsuitable as a direct replacement for potassium bromate.

In the technology of baking bread, salt has the primary purposes of flavor enhancement and strengthening the gluten structure that serves to give bread its shape. However, it is well known that salt has the disadvantages of interfering with yeast growth and, through its dough strengthening effect, limiting the extent to which the dough may rise. This is demonstrated in the common practice within the baking trade of waiting until the final portion of the dough mixing step to add salt as it substantially increases the energy required to achieve a uniform dough. The yeast inhibitory effect occurs at salt concentrations above approximately 1.5%, basis flour. Most commonly, salt is added to a 2% concentration.

For these reasons, there is a substantial need for a potassium bromate replacement product which will (1) increase the volume of the proofed loaf by reducing the effect of salt upon the yeast and (2) add ascorbic acid and salt in such a manner that they can be released slowly during proofing to allow the retention of the increased dough volume and (3) release the bulk of its contained salt and ascorbic acid in the early stages of baking to support he desirable volume expansion and repair the effects of mechanical shock.

DETAILED DESCRIPTION OF THE INVENTION

As used herein, a seeded microcapsule is a microcapsule having an active core surrounded by a shell which in turn has seeding agents disposed therein. Seeding agents are typically in the form of particulate matter, but may also be comprised of liquids solids or gases which are themselves encapsulated by a shell. As used herein, a microcapsule is a capsule having a maximum diameter of 1 micron.

Figure 1:
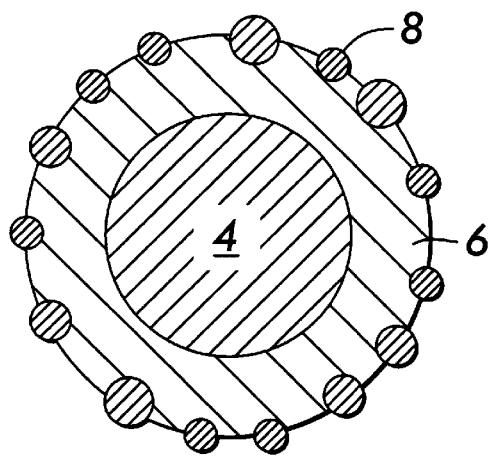
FIG. 1 is a schematic representation of a seeded microcapsule having seeding agents protruding from the shell surface.
Figure 2:
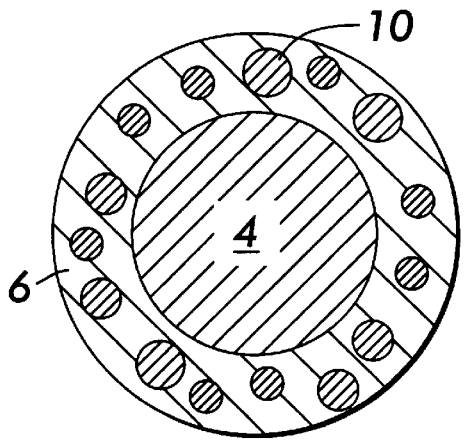
FIG. 2 is a schematic representation of a seeded microcapsule having seeding agents imbedded within the shell material.
Figure 3:
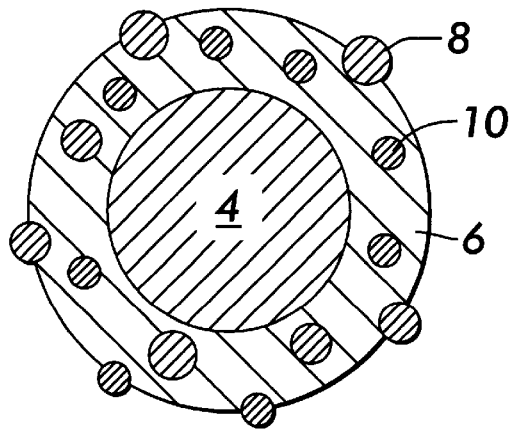
FIG. 3 is a schematic representation of a microcapsule having both imbedded and protruding seeds.

FIG. 1 depicts a microcapsule 2 having a core 4 a shell 6 and protruding seeds 8. In FIG. 2 another microcapsule 2 is shown except that instead of having protruding seeds it has seeds 10 completely imbedded in its shell 6. FIG. 3 shows a microcapsule 2 having a core 4, shell 6, with protruding seeds 8 and imbedded seeds 10.

The seeding agents which are placed in the shell impart unique release or other structural and functional characteristics. The seeds may, for example, act to increase the structural integrity of the shell by thus providing resistance against sheer, pressure, and abrasion. The seeds may also enhance thermal stability to a given material by changing the melting point of the shell or otherwise altering the thermal characteristics of the shell seed combination. Another use of seeds is to alter the weight and/or balance characteristics of the resulting capsule. Seeds can also be used to effect the solubility rate of an otherwise normally insoluble shell, thus acting as a basis for controlling or influencing the release of the core material.

Protruding seeds can affect the manner and degree of resistance between adjacent microcapsules; this can be significant when quantities of microcapsules are in motion, such as when being poured or mixed with other substances. Protruding seeds or a combination of protruding and imbedded seeds can be used to increase the solubility of the seeded shell. The seeds may also be selected so that a pH change of the water into which the microcapsules are placed will affect the capsules' solubility, hence the release of the core material. In this case, the seed material slowly reacts with the shell material to assist in the latter's dissolution. The dissolution of seeds themselves creates passages, channels, or lesions in the shell providing the means by which solvents can come in contact with other seed material, thus permitting the solvent to work its way towards the core material and thereby release it from the shell. Seeding agents whose solubility is effected by pH include ascorbic acid, citric acid, sodium bicarbonate, potassium bicarbonate, and other soluble compounds which are either acidic or basic. Of course, other soluble material may also be employed as means for permitting water or other solvents to reach the shell core.

Figure 4:
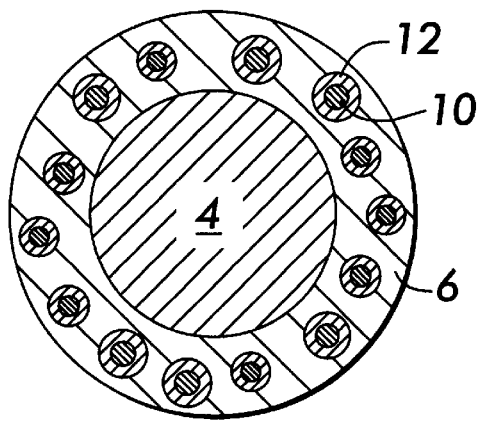
FIG. 4 shows a schematic representation wherein the seeding agent particles imbedded within the shell are themselves encapsulated in a shell.

As shown in FIG. 4, the imbedded seeds 10 may themselves be encapsulated by a shell 12. Although not shown, protruding seeds may also be encapsulated. A microcapsule may also have a combination of imbedded and protruding encapsulated seeds.

Table 1 is a list of materials which may be used as the core material in a seeded microcapsule.

TABLE 1

SOLID PARTICLE CORES

Choline Chloride
Citric Acid
Vitamins including A, B, C, D, K
Sodium Chloride
Potassium Chloride
Acetaminophen
Ibuprofin
Aspirin
Pharmaceutical active agents
Herbicides
Pesticides
Pigments and Colorants
Fumed Silica or Silica Gels
Starches and variations including maltedextrins
Other solid particles

LIQUID CORE SEEDED MICROCAPSULES

Liquids Entrapped in absorbent carriers
Mineral Oil
Vegetable Oils
Pesticides
Herbicides
Fire Retardants
Flavors
Fragrances Table 2 lists various materials which may be used as the shell material for a seeded microcapsule; the materials may also be used as shells for encapsulated seeds.

TABLE 2

Poly urea resins
Epoxy Resins
Melamine resins
Fats and Waxes

Soy fats
Cotton seed
Mono-glycerides
Di-glycerides
Tri-glycerides
Tri-laurins
Palmitic oil based fats
Other fats derived from animal or vegetable bases
Waxes Petroleum based waxes

TABLE 2-continued

Polyethylene waxes
Beeswax
Carnauba wax
Candilita waxes
Polyethylene oxides
Polyvinylacetate based waxes
Meltable polymers and resins
Elastomers Synthetic rubbers
Natural rubber compounds
Natural Polymers Starches
Gelatin
Gums
Bark
Nitrocellulose
Methylcellulose
Ethylcellulose
Other naturally derived polymers
Synthetic Polymers Styrene
Polyethylene
Polyester
Polyureathane
Other synthetic polymers Table 3 lists examples of materials which may be used as seeds.

TABLE 3

| | |
|---|---|
| Sodium Bicarbonate | Citric Acid |
| Potassium Bicarbonate | Fumed Silica |
| Starch | Talc |
| Ascorbic Acid | Silica Gels |
| Cellulosic fibers, particles | Ethylcellulose |
| Methylcellulose | Sodium Chloride |
| Potassium Chloride | Waxes, Paraffin |
| Waxes, Vegetable based | Minerals |
| Calcium Chloride | Calcium Carbonate |

The seeding agent may be selected based upon its solubility characteristics in a particular environment such as upon exposure to various thermal, aqueous, organic, neutral, acidic, basic, gaseous environments or in the presence of enzymes specific to that seeding agent.

Figure 5:
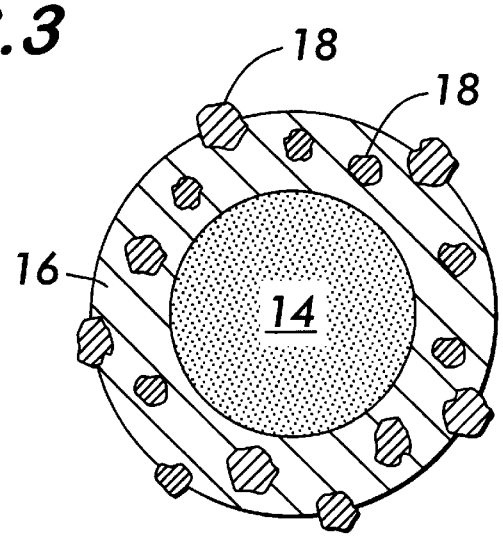
FIG. 5 shows a schematic representation of a seeded microcapsule having a sodium chloride core surrounded by a shell having protruding and imbedded ascorbic acid seeds.

In FIG. 5, an example of a seeded microcapsule having a combination of imbedded and protruding seeds is depicted more particularly, as a microcapsule consisting of a salt core encompassed by an inert thermoplastic shell 14 having imbedded and protruding ascorbic acid seeds, 16 and 18 respectively, is shown. This embodiment of the invention has been designed as a bromate replacement for use in baking.

An example of the invention is directed to a particulate composition for use in baking bromate-free yeast-raised bakery products comprising a particulate core of crystalline sodium chloride having a maximum dimension of 100–500 micrometers encapsulated within an inert thermoplastic shell having a thickness of 10–300 micrometers and a release temperature of 90°–175° F., the shell having randomly dispersed therein 0.25% by weight, basis total particulate composition, of finely divided particles ascorbic acid having a maximum dimensions of 0.5–200 micrometers.

In a secondary aspect, the invention is directed to a dough composition for use in baking bromate-free yeast-raised bread comprising an admixture of flour, salt, yeast, water and the above described encapsulate salt composition in which the weight ratio of unencapsulated salt in the dough to encapsulated salt in the particulate composition is 1:1 to 4:1 and the encapsulated ascorbic acid constitutes 2–220 ppm by weight of the flour component of the dough.

In a further aspect, the invention is directed to a method for baking a bromate-free, yeast-raised bread by a straight-dough method comprising (1) formation of a dough comprising an admixture of flour, water, free salt and yeast, (2) fermenting the dough, (3) dividing and placing the fermented dough into individual pans, (4) proofing the fermented dough and (5) baking the proofed dough, characterized in that the above-described encapsulated salt composition is added to the dough fermenting the dough in such proportions that the weight ratio of unencapsulated salt in the dough to encapsulated salt in the particles is 1:1 to 4:1 and the encapsulated ascorbic acid constitutes 2–220 ppm by weight of the flour content of the dough.

In a still further aspect, the invention is directed to a method for baking a bromate-free, yeast-raised bread by the sponge-and-dough method comprising (1) formation of a sponge comprising an admixture of flour, water and yeast, the sponge containing 10–70% by weight of the total flour content of the bread (2) fermentation of the sponge, (3) formation of a dough by admixing salt, secondary additives and the remainder of the flour with the fermented sponge, (4) proofing the dough and (5) baking the proofed dough, characterized in that the above- described encapsulated salt composition is added to the fermented sponge or dough in such proportions that the weight ratio of unencapsulated salt in the dough to encapsulated salt in the particles is 1:1 to 4:1 and the encapsulated ascorbic acid constitutes 2–220 ppm by weight of the flour content of the dough.

Bread Components and Additives: Except for the encapsulated salt composition of the embodiment, the components of the bakery products in which the invention can be used are conventional and thus well known in the art. For example, the basic constituents of breads are flour, yeast, salt and water. However, as discussed hereinabove, most breads contain one or more secondary additives such as yeast food, calcium propionate, vitamin C (ascorbic acid), sugar, honey, syrups, bakery shortenings, dairy products, egg products, etc. The presence or absence of such secondary bread additives, other than those claimed herein, is not critical with respect to the operability of the invention. That is, the invention is effective in a wide variety of yeast-raised bakery products whether or not they contain any or all of such materials. In addition to bread, the invention can be used in other yeast-raised bakery products such as cake, crackers, pie, pizzas and tortillas.

Encapsulant Shell Material: A wide variety of organic thermoplastic shell materials can be used in the embodiment so long as they are suitable for direct addition to foods. Thus, the composition of the shell component of the invention must be a solid at ambient temperatures, be chemically inert in the presence of all the bread components, be suitable as a food component and have suitable melting properties so that it is released at the appropriate temperature. Such materials include vegetable fats such as mon-, di- and tri-stearates, vegetable oils and wax blends therewith, animal fats such as lard, beef tallow and blends of animal and vegetable fats and hydrogenated derivatives such fats and oils. Also included are waxes such as beeswax, candelilla wax, paraffin ax and microcrystalline wax. Other suitable materials are polysaccharides such as gums, gelatins, alginates and modifications thereof. In addition, polymers such as polyethylene glycols and certain elastomers can be used. These include natural polymers such as carboxymethylcellulose, cellulose acetate phthalate, ethylcellulose, gelatin, gum arabic, starch, succinylated gelatin, proteins and alginates. Other synthetic polymers which can be used as shell materials include poly(vinyl alcohol), and poly (vinyl acetate). Such materials are selected on the basis of their melting point and release characteristics in particular applications. Mixtures of such shell materials can also be used to obtain particular combinations of physical properties.

The amount of ascorbic acid or precursor thereof dispersed in the shell relative to the volume of the shell material (shell loading) is not critical with respect to the functionality of the invention in ordinary baking applications. However, it has been observed that the release of ascorbic acid at equivalent temperature conditions tends to be faster when the volume of ascorbic acid is higher than when a lesser volume of ascorbic acid is used. Thus, the loading level of ascorbic acid in the shell is likely to have an affect on release time.

Formulation and Microencapsulation: The structure of the encapsulated salt particles of the embodiment is illustrated in FIG. 5, which is a schematic representation of the particles. In particular, a crystalline particle of salt 14 is encapsulated within a thermoplastic shell 16 in which are dispersed finely divided particles of ascorbic acid 18. It is preferred that the salt particles which are used in the invention 14 have a maximum dimension of no more 220 micrometers so that they can be easily blended and dispersed in the fermented dough. On the other hand, it is preferred that the salt particles have a minimum dimension no smaller than 100 micrometers because such small particles are more difficult to encapsulate satisfactorily.

It is further preferred that the maximum dimension of the salt particles be in the range of 125–300 micrometers.

The embodiment has been developed primarily for use with sodium chloride because of its overwhelmingly greater use. Nevertheless, the invention is also applicable to the use of other flavoring salts such as potassium chloride, and calcium chloride as well as mixtures thereof with sodium chloride.

It is preferred that the thickness of the organic shell in which the salt particles are encapsulated be at least 10 micrometers and preferably at least 20 micrometers to be assured that the coating is continuous and that it contains no holes. However, the shell thickness should not exceed 300 micrometers and preferably 200 micrometers lest the encapsulated particles become less granular in character and thus are not free flowing. It is, of course, preferred that the particles be free flowing in bulk so that they can be dispersed easily in the dough.

The ascorbic acid is preferred to be of particle size such that it does not exceed about half the thickness of the shell and thus can be randomly dispersed throughout the shell. Though randomly dispersed, ascorbic acid particles can be at the outer surface of the shell, it is, in some applications, preferred that they not protrude because protruding particles would be released too rapidly during the dough fermentation. However, in other applications, it is desirable to have the ascorbic acid protrude through the shell so that dispersion of the salt is accelerated; this can also be used to accelerate, if desired, dispersal of the core. It is also preferred that the ascorbic acid particles not be smaller than 0.5 micrometer because they are difficult to handle. Therefore, the ascorbic acid particles dispersed with the organic shell should be 0.5–200 micrometers in size and preferably 1–100 micrometers. The ascorbic acid particles may be comprised of both large and small particles or other modes of particle size distribution.

The configuration of the dispersed ascorbic acid particles within the shell is important in the practice of the invention in that it determines the slow release character of the ascorbic acid. This phenomenon is not understood fully, but is believed to arise from the fact that discontinuities occur at the shell/particle interfaces, which allow limited release of ascorbic acid by exposure to the moisture content of the dough before the melting point of the shell material has been reached. Thus, ascorbic acid from a small number of particles at or near the outer surface of the shell is slowly released before the bulk of the shell becomes molten.

It will be appreciated that the ascorbic acid derivatives which are precursors of ascorbic acid can be used in the invention as well as ascorbic acid itself. Therefore, compounds such as sodium ascorbate, calcium ascorbate, ascorbyl palmitate, erythorbic acid and sodium erythorbate may also be useful in the practice of the invention. The term "ascorbic acid" as used in the claims is therefore intended to include such ascorbic acid precursors.

The required release temperature of the organic shell material is a function of the proofing and baking temperature. Since the shell materials for use in the invention are heat-released, the melting point of the shell material must be higher than the proofing temperature. In particular, it is preferred that the shell release temperature be at 10°–20° F. higher than the proofing temperature. Thus, if proofing is carried out at 100° F., the release shall temperature should be at least 110° F. and preferably still 120° F. (As used herein, the terms "release temperature" and "melting point" are used interchangeably.) For most applications, the shell release temperature should be 90°–175° F. and preferably 100°–160∨ F.

The amount of ascorbic acid in the shell of the invention particles should be 0.5% by weight, basis total particle weight. If substantially less than 0.5% is used, the oxidative effect is insufficient and the dough will lack strength and have low loaf volume. On the other hand, if more than 5% is used, the oxidative effect is excessive and loaf volume may be diminished.

Though not essential for the practice of the invention, it will be recognized that the shell can have one or more additional secondary additives dispersed therein, for example, other oxidizing agents, sodium diacetate, calcium propionate and the like.

Microencapsulation of the salt can be carried out by any of several conventional microencapsulation methods. A preferred method for carrying out the encapsulation involves the steps of (1) admixing the salt particles into the molten shall material, (2) adding the ascorbic acid to the admixture of salt and shell material and (3) cooling the final admixture to create coated granules which are free flowing. Another technique is use of a fluidized bed. More particularly, the ascorbic acid is suspended in the molten shell material, (2) the salt particles are fluidized and (3) the molten shall material containing ascorbic acid is sprayed into the fluidized salt particles. A still further technique is centrifugal extrusion, as developed by the Southwest Research Institute, San Antonio, Tex.

In the Examples which follow, the encapsulated salt particles are prepared in the following manner:
(1) Hydrogenated cottonseed oil is melted in a jacketed mixing tank;

(2) Fine flake salt is added to the molten cottonseed oil with stirring to obtain a uniform dispersion of the salt in the oil;
(3) While maintaining stirring, ascorbic acid having an average particle size of 3 micrometers is added to the oil/salt dispersion; and
(4) The admixture of oil, salt and ascorbic acid is slowly cooled until the product granulates. The granulated material is then removed from the vessel and screened through a 20 mesh (U.S. Standard) screen.

Ordinarily, it is preferred that the individual particles in bulk be free flowing. However, in some instances it will be desirable to utilize the particles in the form of agglomerated particles or tablets. In those instances, a plurality of particles is agglomerated or tabletted by means of a lowering melting binding agent.

EXAMPLES

Example 1

A quantity of encapsulated salt particles in accordance with the invention and containing by weight 75% fine flake salt, 23% cottonseed oil flake and 2% ascorbic acid is prepared by the following procedure:
1. A jacketed vessel is loaded with the cottonseed oil flake and the vessel is heated to 90°–110° C. to melt the oil flake;
2. The fine flake salt is added to the molten cottonseed oil and the mixture heated to 100°–110° C. for 5 minutes;
3. The heated admixture of oil and salt is mixed at 85° C. for 15–30 minutes after which the temperature is lowered to 60° C.;
4. Finely divided particles of ascorbic acid are added to the oil and salt dispersion and the admixture cooled to 30°–32° C. with continuous agitation; and
5. The cooled admixture is screened through a 20 mesh (U.S. Standard) screen.

Example 2

In a commercial baking line for making whole wheat bread by the sponge-and-dough method, 845 pounds of sponge are prepared containing bromate-free whole wheat flour, wheat gluten, water, yeast food, sodium stearyl lactate, creamed yeast and ascorbic acid tablets. After fermentation, the remainder of the dough components and encapsulated particles made by the method of Example 1 are formed into a second dough, which is mixed into the sponge. The additional dough components are bromate-free whole wheat flour, water, soybean oil, sugar, unencapsulated salt, particles of the composition of the invention containing salt and ascorbic acid, honey, vinegar, calcium propionate, and wheat gluten. The encapsulated salt is equivalent to 0.5% by weight and the encapsulated ascorbic acid is equivalent to 200 ppm, basis dry flour weight. The weight of the final dough is 1461 pounds. After panning and proofing at 90° F. and 85 rh, the dough is baked at 450° F. The resultant bread prepared in accordance with the invention is found to be fully equivalent in every property with the bread prepared by the control method for baking this bread. The control method differs from the experimental run in that the dough contains potassium bromate and free salt replaces the encapsulated salt and ascorbic acid.

Example 3

In commercial baking line for making white bread by the sponge-and-dough method, 1184 pounds of sponge is prepared containing bromate-free white wheat flour, water, yeast, shortening, softener, yeast food and ascorbic acid tablets (44 ppm by weight, basis flour). After fermentation, the remainder of the dough components and encapsulated particles made by the method of Example 1 are formed into a dough and mixed into the sponge. The additional dough components are white wheat flour, water whey unencapsulated salt, particles of the composition of the invention containing salt and ascorbic acid, dough conditioner, syrup, inhibitor, yeast and sodium stearyl lactate. The encapsulated salt is equivalent to 0.5% by weight and the encapsulated ascorbic acid is equivalent to 140 ppm, basis dry flour weight. The weight of the final dough is 1934 pounds. After panning and proofing at 90° F. and 85 rh, the dough is baked at 400°–450° F. The resultant bread is found to be fully equivalent in every property with the bread prepared by the control method for baking this bread. The control method differs from the experimental run in that the dough contains potassium bromate and free salt replace the encapsulated salt and ascorbic acid.

Example 4

In a commercial baking line for making white bread by the sponge-and-dough method, 1191 pounds of sponge is prepared containing bromate-free white wheat flour, water, yeast, shortening, softener, yeast food and ascorbic acid tablets (44 ppm by weight, basis flour). After fermentation, the remainder of the dough components and encapsulated particles made by the method of Example 1 are formed into a dough and mixed into the sponge. The additional dough components are white wheat flour, water, whey, encapsulated salt, dough conditioner, syrup, inhibitor, yeast, sodium stearyl lactate and ascorbic acid tablets. The encapsulated salt is equivalent to 0.5% by weight and the encapsulated ascorbic acid is equivalent to 99 ppm, basis dry flour weight. The weight of the final dough is 1946 pounds. After panning and proofing at 90° F. and 85 rh, the dough is baked at 400°–450° F. The resultant bread is found to be fully equivalent in every property with the bread prepared by a control method for baking the same bread. The control method differs from the experimental run in that the dough contains potassium bromate and free salt replaces the encapsulated salt and ascorbic acid.

In most commercial baking operations, the oven temperature of the baking step is 400°–450° F.; however, the baking temperature for some baked goods may be as low at 350° F., depending on the baking time and the physical characteristics of the baked products in question.

The ratio of unencapsulated salt to encapsulated salt may vary according to the particular baking operation in which the invention is used. In some instances, the weight ratio of unencapsulated salt to encapsulated slat may be as low as 1:1, but is usually preferred to be at least 1.5:1. Nevertheless, the weight ratio of unencapsulated salt to encapsulated salt should not exceed 4:1 and preferably no higher than 3.5:1. A particularly preferred ratio for most bread applications is 3.5:1.

Although the present invention has been described with reference to the particular embodiments herein set forth, it is understood that the present disclosure has been made only by way of example and that numerous changes in details of construction may be resorted to without departing from the spirit and scope of the invention. Thus, the scope of the invention should not be limited by the foregoing specifications, but rather only by the scope of the claims appended hereto.

What is claimed is:

1. A microcapsule for use in baking bromate-free yeast-raised bakery products comprising:
   a core selected from the group consisting of sodium chloride, potassium chloride, calcium chloride, and choline chloride and a mixture of two or more thereof;
   a shell disposed about the core; and
   seeding agents disposed throughout the shell wherein the seeding agents comprise a soluble acidic compound.

2. The microcapsule of claim 1 wherein the seeding agents are encapsulated.

3. The microcapsule of claim 1 wherein the seeding agents comprise ascorbic acid or citric acid or a mixture thereof.

4. A method of conditioning dough comprising the steps of:
   providing microcapsules comprising a core comprising a gluten strengthening agent, a shell disposed about the core, and seeding agents disposed throughout the shell;
   mixing a measured amount of said microcapsules into the dough;
   proofing the dough; and
   baking the dough.

5. The method of claim 4 further comprising the step of releasing a minor portion of the seeding agents into the dough during the proofing step.

6. The method of claim 5 further comprising the step of releasing a major portion of the seeding agents into the dough during the baking step.

7. A method of conditioning dough comprising the steps of:
   providing microcapsules comprising a core selected from the group consisting of sodium chloride, potassium chloride, calcium chloride, and choline chloride and a mixture of two or more thereof, a shell disposed about the core, and encapsulated seeding agents disposed throughout the shell;
   mixing a measured amount of said microcapsules into the dough;
   proofing the dough; and
   baking the dough.

8. The method of claim 7 further comprising the step of releasing a minor portion of the seeding agents into the dough during the proofing step.

9. The method of claim 8 further comprising the step of releasing a major portion of the seeding agents into the dough during the baking step.

10. A dough composition for use in baking comprising flour, salt, yeast, water and a measured amounts of microcapsules comprising a core comprising a salt, an inert organic thermoplastic shell disposed about the core, and seeding agents disposed throughout the shell, wherein said shell possesses melting properties suitable for release of said core during baking.

11. The dough composition of claim 10 wherein the salt is selected from the group consisting of sodium chloride, potassium chloride, calcium chloride, and choline chloride and a mixture of two or more thereof.

12. The dough composition of claim 10 wherein the seeding agents comprise a soluble acidic compound.

13. The dough composition of claim 10 wherein the seeding agents comprise ascorbic acid or citric acid or a mixture thereof.

14. The dough composition of claim 10 wherein the seeding agents are encapsulated.

* * * * *